United States Patent [19]

Trawoger et al.

[11] Patent Number: 5,188,530
[45] Date of Patent: Feb. 23, 1993

[54] PROCESS AND DEVICE FOR PREVENTING MALFUNCTION OF A DENTAL EVACUATION SYSTEM

[76] Inventors: Werner Trawoger, Höttinger Au 60, A-6020 Innsbruck; Bruno Pregenzer, Huebe 30, A-6173 Oberperfuss, both of Austria

[21] Appl. No.: 635,119
[22] PCT Filed: Aug. 23, 1989
[86] PCT No.: PCT/AT89/00073
§ 371 Date: Feb. 25, 1991
§ 102(e) Date: Feb. 25, 1991
[87] PCT Pub. No.: WO90/01909
PCT Pub. Date: Mar. 8, 1990

[30] Foreign Application Priority Data
Aug. 25, 1988 [AT] Austria ................... 2096/88

[51] Int. Cl.⁵ .............................................. A61C 17/06
[52] U.S. Cl. .................................................. 433/92
[58] Field of Search ................................ 433/92, 91

[56] References Cited

U.S. PATENT DOCUMENTS

| 2,895,220 | 7/1959 | Johnston et al. ................ 433/92 |
| 3,746,033 | 7/1973 | Keiper, II ........................ 433/92 |
| 4,054,998 | 10/1977 | Hesselgren ...................... 433/92 |
| 4,245,989 | 1/1981 | Folkenroth et al. ............. 433/92 |

FOREIGN PATENT DOCUMENTS 0023036 7/1980 European Pat. Off. .
0237708 1/1987 European Pat. Off. .
8603669 7/1986 PCT Int'l Appl. .

OTHER PUBLICATIONS

Instructions for the use of anti-foaming pills, Cattani S.p.A., Parma, Italy date—prior to Aug. 1988.

Primary Examiner—John J. Wilson
Attorney, Agent, or Firm—Lorusso & Loud

[57] ABSTRACT

To prevent, as far as possible, malfunction of a dental evacuation system, portions of a free-flowing additive are added at intervals to at least one constituent of the liquid-solids mixture. This is repeated several times during each period of operation of the evacuation system within the first evacuation section, which includes the separator (1). The additive added in portions may be, for example, a disinfectant, a cleaning agent and/or an anti-foam agent.

14 Claims, 5 Drawing Sheets

PROCESS AND DEVICE FOR PREVENTING MALFUNCTION OF A DENTAL EVACUATION SYSTEM

The invention concerns a process and a device for preventing functional breakdowns in a dental suction unit, in which a mixture of a liquid and solid matter is suctioned out of the patient's mouth using a vacuum and goes through an initial suction line that ends at a trap, where the air is separated out and goes to the vacuum pump. The trap also preferably separates the liquid from the solid matter, which is caught in a removable collection container, and the liquid is drained off.

BACKGROUND OF THE INVENTION

Dental suction units, as described for example in WO-A-86/03669, are plagued with special problems because of the composition of the mixture to be suctioned and treated (blood, saliva, water, pus, tooth material, residues of amalgam, etc.), which can lead to serious functional breakdowns. These problems come from cleaning and disinfecting the part of the system through which the mixture flows, which is hereafter called the initial suction line, and also from the fact that blood mixing with the hydrogen peroxide constantly used in dentistry can cause an intensive build-up of foam, which shuts down the system, since the outlet to the vacuum from the trap must naturally be safeguarded against foreign matter flowing through it. The foam that is created has a particularly great stability, and dissolving it automatically takes several hours. On the other hand, dissolving, cleaning and sterilizing a trap is not only time-consuming, but is also an unhygienic activity, since the mixture has a very high concentration of bacteria.

We know how to simplify at least the cleaning or disinfection from EP-B-23036. In it, the outflow duct for the trapped, unseparated mixture of liquids and solid matter has a siphon that siphons off a cleaner from a cleaner container with a rinsing duct at the end whose other end can be connected to a suction hose. The unit can be cleaned or disinfected at the end of a working period, usually at the end of the daily office hours, by connecting the suction hose to the rinsing duct and hooking up the suction unit so that the additive to be added then flows through the initial suction line.

While work is going on, it is hardly possible to add the additive since the equipment makes it impossible for the dentist to work in the interim. According to EP-A-237708, on the other hand, the trap, which has an extraction pump for the trapped liquid and preferably also a centrifuge, is fitted with a propeller, which is between the air trap and the liquid collection space. The foam that builds up is supposed to be destroyed using the propeller. This may work satisfactorily when the pump is running, but when the pump is turned off, the propeller does not prevent the undisturbed, built-up foam from passing through. (The foam build-up takes place gradually, even when the unit is temporarily stopped.) On the other hand, the foam that has gotten into the air trap prevents the suction unit from being turned on, which causes the breakdown mentioned at the beginning. Adding a cleaner or disinfectant is not described in that publication.

SUMMARY OF THE INVENTION

The invention is based then on the idea that the prevention of foam build-up or at least its fast, direct destruction would practically rule out functional breakdowns caused by foam, and that more frequent cleaning and disinfection would also prevent at least those functional breakdowns that result from excess accumulation of contaminants.

The task of the invention is therefore to create a process and a device to prevent such functional breakdowns, in order, if possible, to extend the maintenance intervals so that the corresponding maintenance work will be needed when the whole unit is serviced or when the collection container is emptied, etc.

The invention does this by adding a free-flowing additive to at least one component of the mixture within the initial suction line at intervals during each period that the suction unit is operating.

Free-flowing additives are understood to be any agents suitable for eliminating at least one of the problems listed. Thus, a disinfectant and/or a cleaner and/or an anti-foaming agent can be added in portions. Such additives, and anti-foaming agents as well, are known as such and are available on the market, so that there is no need to go into greater detail about them.

The concept of preventing the creation of foam or destroying it with an added anti-foaming agent is therefore unique to the invention.

Thus the additive will preferably consist of a mixture of all agents that can be used or are needed, which also expands the range of usable cleaners or disinfectants from which to choose, since high-foaming agents can also he used because the foam build-up is eliminated anyway by an anti-foaming agent.

The additive or mixture of additives is added within the initial suction line defined above, which begins at the mouthpiece. In a new suction unit, it can be added there, preferably; if a system that already has a cleaning system according to EP-B-23036 mentioned above is being refitted or expanded, the process in the invention can be limited to the addition of an anti-foaming agent. This, then, preferably takes place at the end of the first suction line, in the trap itself. If the solid matter is sedimented in the collection container, it is preferable to provide for the anti-foaming agent to be added in portions to the liquid collecting above the sedimented solid matter.

The additive can be added at regular intervals during the operating period, for example, every quarter of an hour around the clock. In one preferred version, however, the additive is preferably added upon each transition from a working phase to a resting phase. Such transitions take place frequently enough during the operating period, approximately one hundred to two hundred times during a full day of office hours. Since the anti-foaming agents in particular are still effective when highly diluted, when this process is being carried out, the portion of the additive that is being added can be limited to a few drops, so that there is no excessive use.

In one preferred version, it is added during the resting phase and is released when the pressure in the suction unit drops, or each time the mouthpiece is hung up.

A device for carrying out the process in the invention includes, according to the invention, a container to hold a supply of the additive, a line coming out of the container that has a dosage device on it, and an interval-control device for adding a portion from the supply each time.

The intervals can be controlled by a control unit, wherein the intervals may be equal or unequal. But this requires additional expense for parts, if the control is electrical or electronic.

Control is simplified by the fact that the dosage device has a valve unit controlled by the vacuum pressure, since the control impulses required are given by the frequent switching.

One preferred version of a valve unit consists, for example, of the fact that it includes two return valves and a dosage pump arranged between them that can operate either electrically or by changes in pressure. One inexpensive design for the return valves provides that they be in the form of flap valves, at least one of which is weighted to return. This flap valve then opens upwardly, and the valve flap touches the supporting body, especially a support ball. A reciprocating pump, wherein a diaphragm pump is preferably used that does not need its own piston seal, is especially suitable for the dosage pump.

Thus the diaphragm can be made to move advantageously by the negative pressure in the suction unit, and the return movement can be brought about by a return spring or by gravitational force.

Another version of the device provides for the container to be arranged above the dosage device, which has a stop valve in the duct, wherein the additive flows out of the container under the influence of gravity. A magnetic valve or, preferably a valve controlled by negative pressure, can be used as the stop valve.

The suction action of a suction unit is generally very high, and an operating pressure of 0.1 bar can easily be reached. It is therefore insignificant if slight quantities of outside air get into the suction line. For this reason, preferably, there is an design in which the outlet of the dosage device is arranged under a filling funnel that is under atmospheric pressure, whose spout empties into the negative-pressure system within the initial suction line. Since the amount of the dose is only a few drops, the cross section of the spout can be kept very small, but the capillary forces, which could prevent the outflow under the force of gravity, cannot cause breakdowns, since each time the suction unit is turned on, the portion of additive that remains in the filling funnel or in this spout is sucked into the initial suction line.

Another version provides for the conduit from the container to be airtight and to empty into the negative-pressure system of the suction unit within the initial suction line, and for it to have a stop valve as the dosage device. According to this design, the portions released by the stop valve, activated electrically or by negative pressure, are sucked directly out of the container. In the designs described until now, the additive is under normal air pressure in the container. But it is also possible to integrate the container into the negative-pressure system of the suction unit and to equip it with a lift-type stand pipe, wherein the pressure difference specified by the angle of the stand pipe is sufficient to dispense the portion to be dispensed from the supply.

BRIEF DESCRIPTION OF THE DRAWINGS

The invention will now be described in more detail below, using the Figures in the enclosed drawings, but it is not limited to them.

DESCRIPTION OF THE PREFERRED EMBODIMENT

Figure 1:
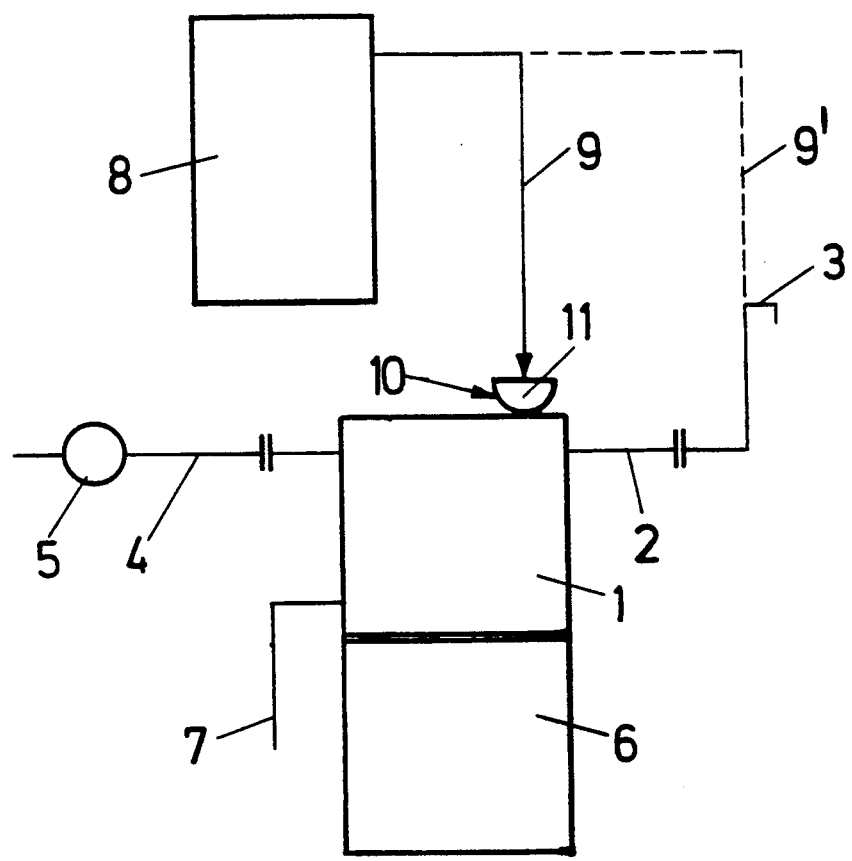
FIG. 1 shows a schematic representation of a preferred version of the invention.

A dental suction unit has, according to FIG. 1, a vacuum pump 5, whose vacuum duct starts at a mouthpiece 3 of a manual suction device. The suction duct leading to the pump 5 has an initial section 2 between the mouthpiece 3 and the trap 1. In the trap 1, there is a separation of the mixture of liquid and solid matter vacuumed through the mouthpiece 3, wherein the separated vacuum goes to the pump 5 via a second section 4 of the suction duct, the liquid leaves the trap 1 via the outflow duct 7, and the solid matter is collected in a removable collection container 6, in which it is preferably sedimented. A container 8 is used for holding a cleaning and/or disinfecting and/or foam-destroying additive, and has a conduit 9 in which a dosage device 10 is contained, by means of which the additive is conveyed in portions of a few drops into an initial suction line of the system. This initial suction line includes the part of the suction unit that the mixture flows through, i.e., it includes the mouthpiece 3 and the trap 1. The additive can also be inserted at another site on the initial suction line, as shown by the broken line 9'.

Figure 2:
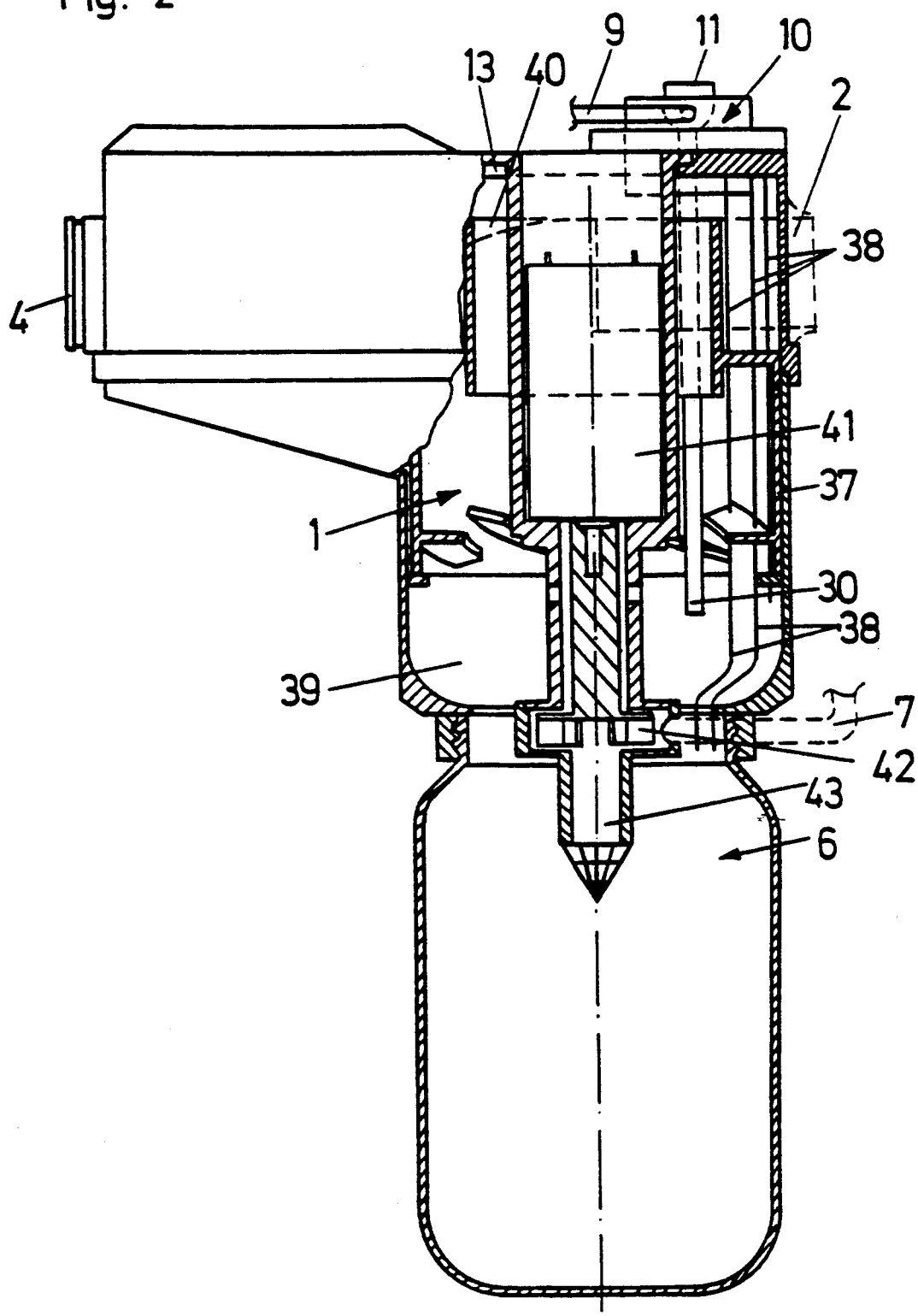
FIG. 2 a vertical section through one example of a version with a dosage device arranged on the trap.

The trap shown in FIG. 2 has an air-collection chamber 40 on the input side of the initial section 2 of the suction line, from which the clean suctioned air goes via part of the trap 1, not shown in detail, to the connection for the section 4 of the suction line. Within the chamber 40, there is a motor 41, which has a pump 42, from which the outflow line 7 goes to carry off the separated liquid. Assigned to the pump 42 is a vacuum pipe 43 projecting into the removable collection container 6, and there are filling-status sensors 38 that end at the height of the pump 42 and switch the pump 42 on and off. A third filling-status sensor 37 ends somewhere over the pump 42 and turns off the suction unit if this level is exceeded and prevents liquid from going to the second section 4. The sensor 37 also reacts naturally to the foam created in the liquid-collection space 39.

The dosage device 10 for the additive coming through the duct 9 is placed in a cover 13 of the trap 1.

Figure 3:
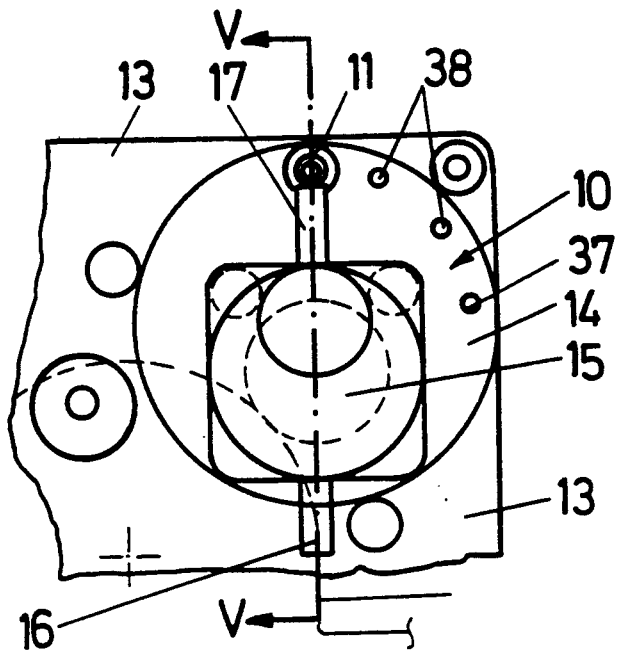
FIG. 3 an overview of the design in Fig 2.
Figure 4:
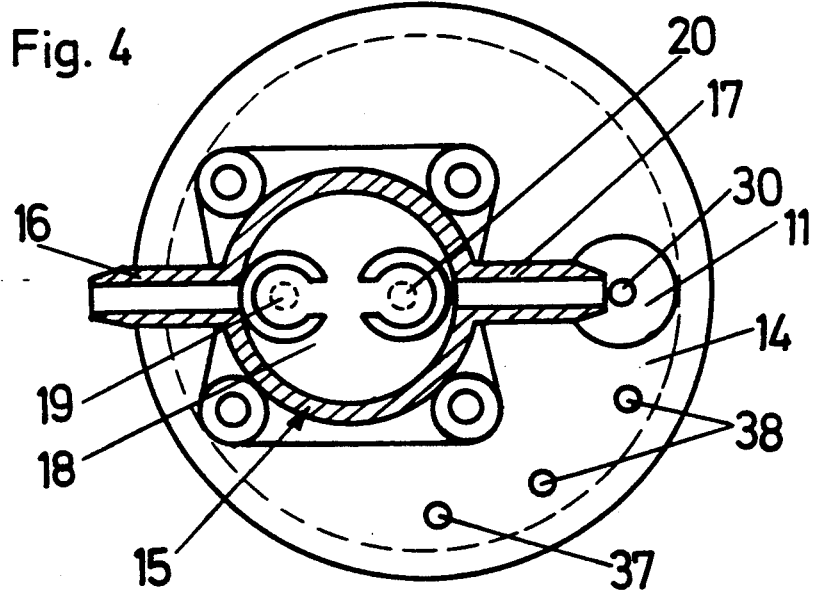
FIG. 4 a section along the line IV—IV in FIG. 5.
Figure 5:
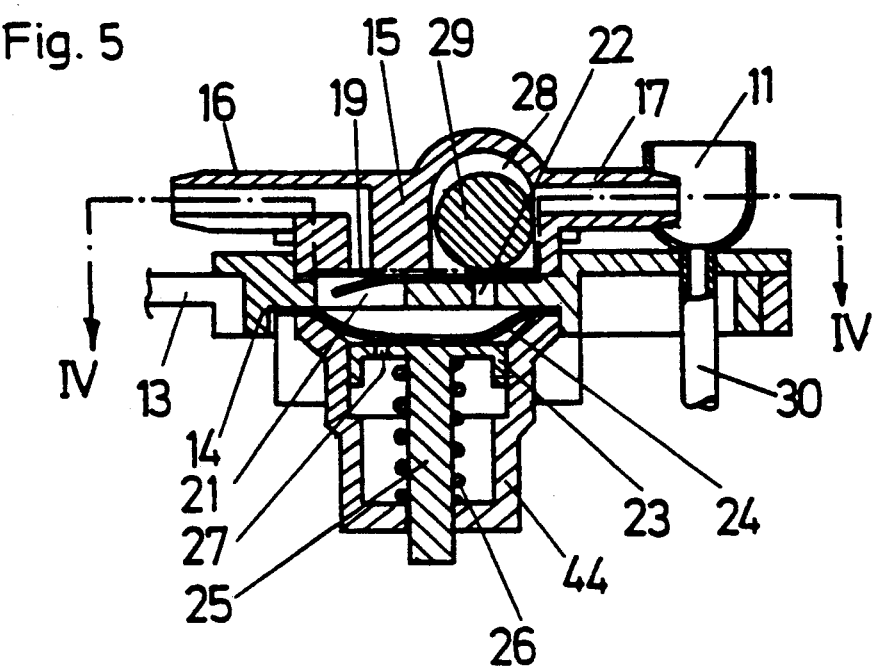
FIG. 5 a section along the line V—V in FIG. 3.

As can be seen from the details in FIGS. 3 to 5, the dosage device 10 has a frame 14, which has a valve 15 with an inlet 16 and an outlet 17. The valve 15 and the frame 14 hold in place a diaphragm 18 that has two valve flaps 19, 20, which lock or release the openings 21, 22 in the basic frame 14. The valve flap 19 locks the inlet 16 and opens below into a dosage space 23, which is surrounded by a pump diaphragm 24 of the dosage pump. The pump diaphragm 24 is stretched between the frame 14 and a counterpart 44 and is thus inside the trap 1, wherein screws, not shown, attach the valve 15, the frame 14 and the counterpart 44 to one another. A moveable piston 25 admitting the pump diaphragm 24 from the outside is located in the counterpart 44 and has an opening 27 with a return spring 26.

The valve flap 20, as part of the outlet valve opens upward into an outlet space 28, in which a ball 29 is arranged as a loading weight of the valve flap 20. The outlet 17 of the dosage device 10 goes into a filling funnel 11 open to the atmosphere, which is arranged in the frame 14, and to which an outflow pipe 30 is connected which projects into the liquid collection space 39.

The apportioning of the pre-supplied additive in the container 8 now takes place under the influence of the pressure changes in the suction unit as follows: When the suction unit is turned off, the pump diaphragm 24 presses on the lower side of the frame 14 via the return spring 26, and the additive in the duct 9 is thereby prevented from flowing through by the dosage device 10. When the suction unit is turned on, it is pulled down against the return spring 26 by the negative pressure outside on the pump diaphragm 24, whereupon the additive in the dosage space 23 flows through the open valve flap 19. The valve flap 20 is closed and the weight of the ball 29 puts pressure on it. A small, harmless quantity of outside air goes into the trap 1 through the filling funnel 11.

As soon as the suction unit is turned off in its cabinet by hanging up the mouthpiece 3, the piston 25 moves up via the return spring 26 and presses the pump diaphragm 24 on the lower part of the frame 14. The valve flap 19 closes and the valve flap 20 opens, removing the ball 29. The portion of additive, which consists of a few drops, (the picture in FIGS. 4 and 5 corresponds to double the natural size) goes via the outlet 17 into the filling funnel 11, from which the liquid in the liquid collection space 39 is added via the outflow pipe 30. If the additive is an anti-foaming agent, the foam build-up is prevented and any foam created is destroyed. If the additive is a disinfectant, germs contained in the separated liquid will be rendered harmless.

When the unit is turned on again, any remaining residues of the portion just fed in are suctioned off via the suction effect from the open filling funnel 11, so that the portion is completely added by a capillary action of the outflow pipe 30. The pump diaphragm 24 is pressed down by the negative pressure under compression of the return spring 26, so that the dosage space 23 is enlarged, whereby the next portion flows out of the container 8 via the valve flap 19 that is opening. The closed valve flap 29 pressed down by the ball 29 prevents the aspiration of outside air via the outlet 17. In this way, each time the suction unit is turned off, i.e., at the beginning of a resting phase, a portion of the additive goes into the inside of the trap.

Figure 6:
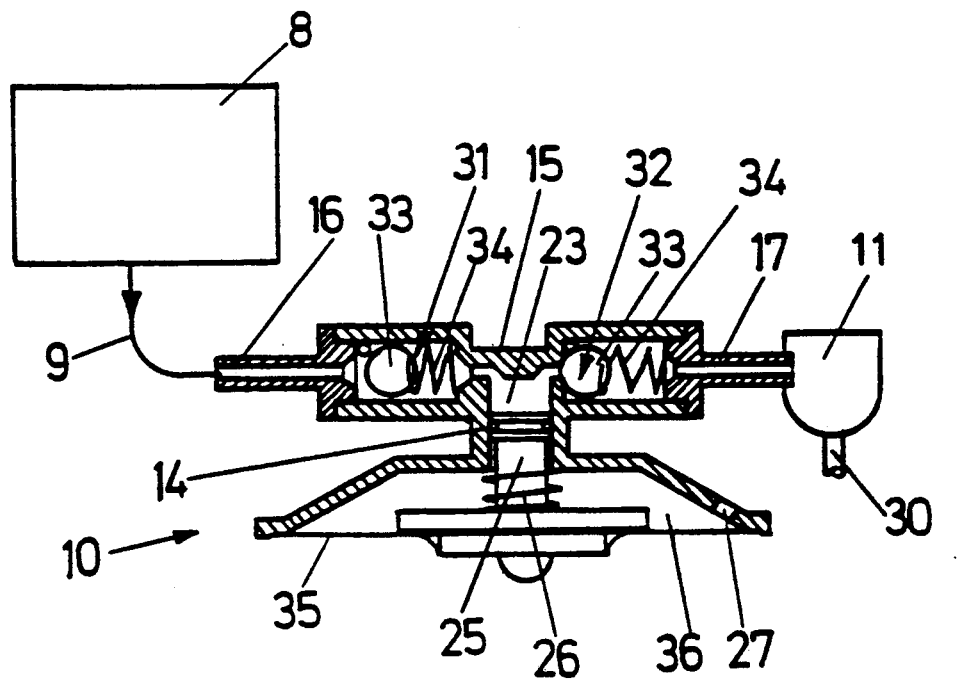
FIG. 6 a section similar to FIG. 5, through another design of a dosage device.

The design shown in FIG. 6 of the dosage device 10 works in the opposite way, i.e, the dosaged portion goes into the trap 1 each time the suction unit is turned on, that is, at the beginning of the work phase. In this design, return valves 31, 32 with ball-shaped valves 33 and return springs 34 are provided as valves, and the dosage space 23 is bordered by pistons 25 sealed directly into the frame 14, to which the return spring 26 is in turn assigned. The dosage device, according to FIG. 6, is also suitable for building into the cover 13 of the trap, but can also be mounted in another place as a closed part. In this design, the application of negative pressure to the opening 27 in an otherwise closed suction space 26 lifts a diaphragm 35 to which the piston 29 is attached and when the negative pressure is lifted, it is moved back to the place shown by the spring 26 or by its own weight. The dosage of the additive takes place, depending on the design, according to FIGS. 3 to 5.

As just mentioned, using a change in pressure to activate the dosage device has a special advantage, since additional control devices are unnecessary. However, the dosage device could also be activated by a magnetic valve or even mechanically, and in these designs, other intervals could be used as the switching intervals of the suction unit. Thus, portions could also be added at regular intervals by using a clock relay. An example of such a design is shown schematically in FIG. 7. Here, the container 8 is placed above the trap 1, so that the additive can flow into the filling funnel 11 via the duct 9 by the force of gravity, as soon as a stop valve 12 of any kind is opened and closed again, depending on the time or the amount of flow, as in counting the drops. In this version, it can be added at any time desired.

Figure 8:
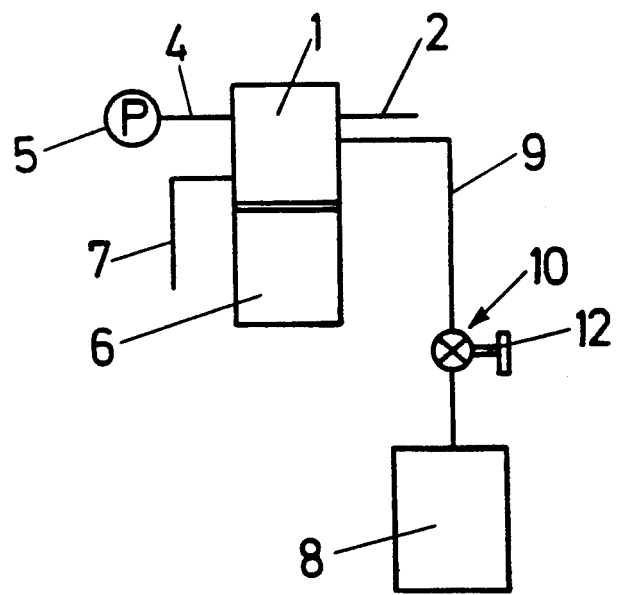

Another design that also doses by means of negative pressure is shown in FIG. 8, wherein here the additive is aspirated out of the container lying under the trap 1 by the negative pressure, as soon as the stop valve 12, which is in turn controlled by the time or the amount of flow that the dosage device 10 forms, opens and closes. According to this design, dosage can take place at any time during a work phase.

Figure 7:
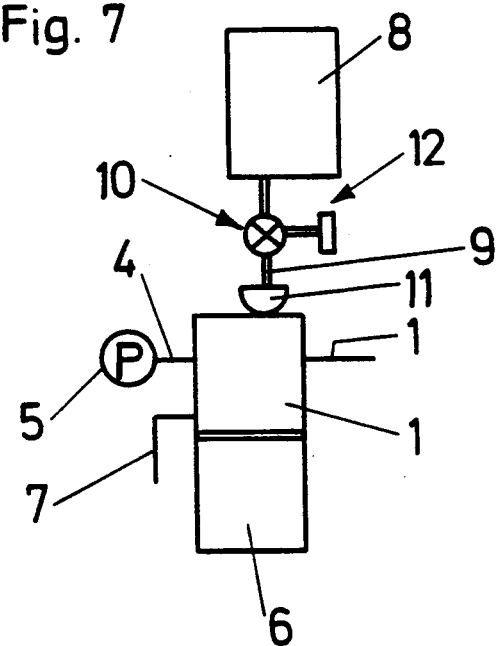
FIGS. 7 and 8 schematic representations of two other versions of the invention.

Coming back to FIG. 1, it is also possible to have the dosage devices, primarily of the designs described in FIGS. 6 to 8, empty at any place in the initial suction line, as shown by the broken line 9'. If the container 8 also contains a cleaner and/or disinfectant as the additive, then it is an advantage to add it directly at the mouthpiece 3, whereby the whole initial suction line coming into contact with the liquid and solid matter can be cleaned, disinfected and provided with an anti-foaming agent.

We claim:

1. A process for preventing functional breakdowns in a dental suction unit by preventing the build-up of foam in the suction unit during dental treatment, comprising:
    a) inserting a suction nozzle of a suction line into a patient's mouth whereby said suction line has a first and a second section, wherein said suction nozzle is in said first section,
    b) creating a negative pressure in said suction line through the attachment o said second section to a suction pump,
    c) aspirating the contents of a patient's mouth into said first section whereby said contents contain a mixture of solids and liquid material,
    d) routing said mixture from said first section to a separator dividing said first and second sections of said suction line, whereby said separator comprises an air separating chamber and a mixture separating chamber,
    e) separating air from said mixture through said air separating chamber,
    f) collecting said mixture in said mixture separating chamber,
    g) adding at definite intervals to said mixture aspirated through said first section of said suction line, a free-flowing additive containing an anti-foaming agent,
    h) repeating steps a)-f) without risk of unit malfunction due to the accumulation of substances in the unit.

2. The process of claim 1, wherein said free-flowing additive of step g) contains a disinfectant.

3. The process of claim 1, wherein said free-flowing additive of step g) contains a cleaning agent.

4. The process of claim 1, wherein said free-flowing additive of step g) is added within said suction nozzle.

5. The process of claim 1, wherein said free-flowing additive of step g) is added into the mixture collecting chamber of the separator.

6. The process of claim 1 wherein said free-flowing additive of step g) is added at each transition between a working phase and a resting phase of the pump.

7. The process of claim 1, wherein the addition of said free flowing additive of step g) is triggered by cancellation of the negative pressure in the suction unit.

8. A suction unit capable of continuing dental treatment without risk of unit malfunction due to the presence of certain substances, said unit comprising;
- a suction line having a first section and a second section, wherein said first section is adapted for use in a patient's mouth,
- pump means connected to said second section of said suction line for creating a negative pressure therein thereby effecting aspiration of a mixture of solids and liquids from a patient's mouth into said suction line,
- separating means contained in said suction line, for directly receiving an additive and said contents contained in said suction line, whereby said mixture is collected and air is separated out to return to said pump means,
- container means for containing a supply of an additive capable of counteracting the formation of substances causing unit malfunction,
- dosage means for defining portions of said additive to be added to said first section for combination with said mixture, said dosage means comprising a duct connecting said container with said first section of said suction line, and a valve unit controlled by vacuum pressure, wherein said valve unit further comprises two return valves with a dosage pump therebetween,
- interval-control means for controlling said dosage means whereby said dosage means is effected in intervals,
- such that the formation of substances causing unit malfunction is prevented.

9. The suction unit of claim 8, wherein said return valves are flap valves, whereby one of said valves is weighted.

10. The suction unit of claim 8, wherein said dosage pump is a diaphragm pump.

11. The suction unit of claim 8, wherein said duct is airtight and said dosage means further comprises a stop valve.

12. A suction unit capable of continuing dental treatment without risk of unit malfunction due to the presence of certain substances, said unit comprising;
- a suction line having a first section and a second section, wherein said first section is adapted for use in a patient's mouth,
- pump means connected to said second section of said suction line for creating a negative pressure therein thereby effecting aspiration of a mixture of solids and liquids from a patient's mouth into said suction line,
- separating means contained in said suction line, for directly receiving an additive and said contents contained in said suction line, whereby said mixture is collected and air is separated out to return to said pump means,
- container means for containing a supply of an additive capable of counteracting the formation of substances causing unit malfunction,
- dosage means for defining portions of said additive to be added to said first section for combination with said mixture, said dosage means comprising a duct having a stop-valve placed therein, said duct connecting said container with said first section of said suction line,
- wherein said container means is placed at a height above said dosage means, such that said additive flowing from said container to said dosage means is gravity assisted,
- interval-control means for controlling said dosage means whereby said dosage means is effected in intervals,
- such that the formation of substances causing unit malfunction is prevented.

13. A suction unit capable of continuing dental treatment without risk of unit malfunction due to the presence of certain substances, said unit comprising;
- a suction line having a first section and a second section, wherein said first section is adapted for use in a patient's mouth,
- pump means connected to said second section of said suction line for creating a negative pressure therein thereby effecting aspiration of a mixture of solids and liquids from a patient's mouth into said suction line,
- separating means contained in said suction line, for directly receiving an additive and said contents contained in said suction line, whereby said mixture is collected and air is separated out to return to said pump means,
- container means for containing a supply of an additive capable of counteracting the formation of substances causing unit malfunction,
- dosage means for defining portions of said additive to be added to said first section for combination with said mixture, said dosage means comprising a duct connecting said container with said first section of said suction line, and an outlet arranged in a filling funnel which is under atmospheric pressure, said funnel opening into said first section of said suction line,
- interval-control means for controlling said dosage means whereby said dosage means is effected in intervals,
- such that the formation of substances causing unit malfunction is prevented.

14. A process for preventing functional breakdowns in a dental suction unit by preventing accumulation of substances causing unit malfunction during dental treatment, comprising:
- a) inserting a suction nozzle of a suction line into a patient's mouth whereby said suction line has a first and a second section, wherein said suction nozzle is in said first section,
- b) creating a negative pressure in said suction line through the attachment of said second section to a suction pump,
- c) aspirating the contents of a patient's mouth into said first section whereby said contents contain a mixture of solid and liquid material,
- d) routing said mixture from said first section to a separator dividing said first and second sections of said suction line, whereby said separator comprises an air separating chamber and a mixture separating chamber,
e) separating air from said mixture through said air separating chamber,
f) collecting said mixture in said mixture separating chamber,
g) adding at definite intervals to said suction nozzle a free-flowing additive containing an anti-accumulating agent,
h) repeating steps a)–f) without risk of unit malfunction due to the accumulation of substances in the